US006232474B1

(12) United States Patent
Brandenburg et al.

(10) Patent No.: US 6,232,474 B1
(45) Date of Patent: *May 15, 2001

(54) PROCESS FOR THE PREPARATION OF α-METHYLENELACTONES AND α-SUBSTITUTED HYDROCARBYLIDENE LACTONES

(75) Inventors: Charles Brandenburg, Wilmington, DE (US); Randal King, Kennett Square, PA (US); Leo E. Manzer, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/536,350

(22) Filed: Mar. 27, 2000

Related U.S. Application Data

(60) Provisional application No. 60/126,883, filed on Mar. 30, 1999, and provisional application No. 60/126,884, filed on Mar. 30, 1999.

(51) Int. Cl.[7] ........................ C07D 307/02; C07D 313/00
(52) U.S. Cl. ............................ 549/295; 549/266; 549/273
(58) Field of Search ....................................... 549/266, 273, 549/295

(56) References Cited

U.S. PATENT DOCUMENTS 5,166,357  11/1992  Orlek et al. ........................... 514/299

FOREIGN PATENT DOCUMENTS

| 295553 | 6/1988 | (EP) . |
| 366304 | 10/1989 | (EP) . |
| 10-120672 | 5/1998 | (JP) . |
| 10298172 | 11/1998 | (JP) . |

OTHER PUBLICATIONS

Martin, J., Et Al., A New Method for the Synthesis of a–Methylenebutyrolactones, Chemical Communications, 1970, 27.

Watts et al., J. Chem. Soc. Chem. Comm. 27 (1970).

A. W. Murray et al., Synthesis, Jan. 1985, p. 35–38.

Primary Examiner—Amelia Owens

(57) ABSTRACT

This invention pertains to a process for making α-methylenelactones and α-substituted hydrocarbylidene lactones. The present invention obtains high yields of α-methylene-γ-butyrolactone by heating γ-butyrolactone and formaldehyde in the presence of a base.

43 Claims, No Drawings

PROCESS FOR THE PREPARATION OF α-METHYLENELACTONES AND α-SUBSTITUTED HYDROCARBYLIDENE LACTONES

This application claims the benefit of U.S. Provisional Application Nos. 60/126,883 and 60/126,884, both filed Mar. 30, 1999.

FIELD OF THE INVENTION

This invention is in the field of synthetic organic chemistry. This invention pertains to a method to produce α-methylenelactones and α-substituted hydrocarbylidene lactones. More specifically, this invention pertains to a simple, efficient and economic method to produce α-methylene-γ-butyrolactone from γ-butyrolactone.

TECHNICAL BACKGROUND OF THE INVENTION

α-Methylenelactones have been the subject of intensive synthetic studies. Specifically, the α-methylene-γ-butyrolactone group is an important structural feature of many sesquiterpenes of biological importance. In addition, α-methylene-γ-butyrolactones are regarded as potential key monomers in both homopolymers and copolymers. Currently the cost of α-methylene-γ-butyrolactone is too high to warrant commercial production of the resulting polymers. Some of the current synthetic routes suffer from low yields, byproducts formation and expensive starting materials. The instant invention has overcome these problems and high yields of α-methylene-γ-butyrolactone are obtained by heating γ-butyrolactone and paraformaldehyde in the presence of a base such as cesium carbonate or potassium carbonate.

An early synthesis of α-methylene-γ-butyrolactone involved two steps (Martin et al., *J. Chem. Soc.* D 1:27 (1970)). The first is carboxylation of γ-butyrolactone with methyl methoxymagnesium carbonate (Stiles' reagent) to produce the acid. Next, the acid is briefly treated with a mixture of aqueous formaldehyde and diethylamine, followed by a separate treatment of the crude product with sodium acetate in acetic acid. The first step requires 6–7 hours and affords almost quantitative yields, whereas the second step can be accomplished in less than 30 minutes but with yields of only 50%.

Murray et al. (*Synthesis* 1:35–38 (1985); see also U.S. Pat. No. 5,166,357) disclose a route to α-methylene-γ-butyrolactone that also involves a two-step sequence consisting of the reaction of γ-butyrolactone with ethyl formate in the presence of base, followed by refluxing the resulting α-formyl-γ-butyrolactone sodium salt under nitrogen with paraformaldehyde in tetrahydrofuran. Distillation affords the desired α-methylene-γ-butyrolactone as a colorless oil. This reaction sequence can best be explained by formyl transfer from carbon to oxygen followed by elimination of carboxylate anion.

Essentially all approaches to α-methylene-γ-butyrolactone are liquid-phase processes. One exception is the vapor-phase process described in JP 10120672. Production of α-methylene-γ-butyrolactone comprises subjecting γ-butyrolactone or an alkyl-substituted γ-butyrolactone, in which one or more hydrogen atoms at the β- or γ-position of the γ-butyrolactone are substituted with $C_1$–$C_{18}$ alkyl groups, to a gaseous phase catalytic reaction using a raw material gas containing formaldehyde or its derivative in the presence of a catalyst. Molecular oxygen is preferably added to the raw material gas and the catalyst is preferably silica alumina catalyst. Specifically, a gaseous mixture of γ-butyrolactone, formaldehyde, water, nitrogen and oxygen was passed through a reactor packed with Wakogel C-200, pretreated with an aqueous potassium hydroxide solution and heated, at 330° C., to afford α-methylene-γ-butyrolactone at a conversion of 35.5% and a selectivity of 46.9%.

Although the above methods for the production of α-methylene-γ-butyrolactone are useful, they are time consuming and are multipart processes. The present method represents an advance in the art by offering a process that is a single step, run at low temperature with high yields and good selectivity.

SUMMARY OF THE INVENTION

The instant invention relates to a process for preparing α-methylenelactones of Formula II comprising heating lactones of Formula I and formaldehyde in the presence of a base:

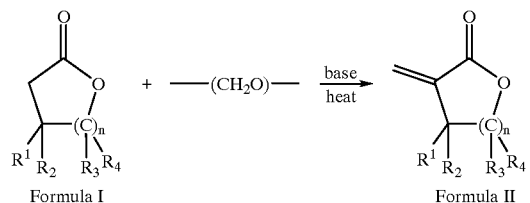

wherein, n=1–11;

$R^1$, $R^2$, $R^3$ and $R^4$, taken independently are hydrogen, hydrocarbyl or substituted hydrocarbyl, $C_1$–$C_{18}$ unsubstituted or substituted alkyl, unsubstituted or substituted alkenyl, unsubstituted or substituted cylcoalkyl, unsubstituted or substituted cylcoalkyl containing at least one heteroatom, unsubstituted or substituted aromatic ring, and unsubstituted or substituted aromatic ring containing at least one heteroatom.

The invention further provides a process for the preparation of compounds of Formula II wherein any two of $R^1$, $R^2$, $R^3$ and $R^4$ are members of a ring structure selected from the group consisting of, unsubstituted or substituted cylcoalkyl, unsubstituted or substituted cylcoalkyl containing at least one heteroatom in the ring, unsubstituted or substituted aromatic ring, and unsubstituted or substituted aromatic ring containing at least one heteroatom in the ring.

In another embodiment of the invention, the invention provides a process for preparing α-substituted hydrocarbylidene lactones of Formula III comprising heating lactones of Formula I and a formaldehyde derivative in the presence of a base

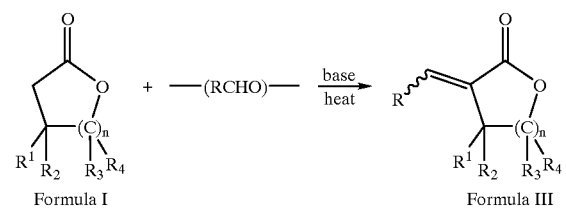

wherein, n=1–11;

R is hydrocarbyl or substituted hydrocarbyl; and $R^1$, $R^2$, $R^3$ and $R^4$ taken independently are hydrogen, hydrocarbyl or substituted hydrocarbyl, $C_1$–$C_{18}$ unsubstituted or substituted alkyl, unsubstituted or substituted alkenyl, unsubstituted or substituted cylcoalkyl, unsubstituted or substituted cylcoalkyl containing at least one heteroatom, unsubstituted or substituted aromatic ring, and unsubstituted or substituted aromatic ring containing at least one heteroatom.

The invention further provides a process for the preparation of compounds of Formula II wherein any two of $R^1$, $R^2$, $R^3$ and $R^4$ are members of a ring structure selected from the group consisting of, hydrocarbyl or substituted hydrocarbyl, $C_1$–$C_{18}$ unsubstituted or substituted alkyl, unsubstituted or substituted alkenyl, unsubstituted or substituted cylcoalkyl, unsubstituted or substituted cylcoalkyl containing at least one heteroatom in the ring, unsubstituted or substituted aromatic ring, and unsubstituted or substituted aromatic ring containing at least one heteroatom in the ring.

In both processes the base is metal carbonate, oxide, hydroxide or phosphate or mixtures thereof and may be supplied as a homogeneous or heterogeneous catalyst. The process is conducted at a temperature range of at least about 70° C. and a pressure less than or equal to 2000 psi. The reaction may optionally run at higher temperatures, at about 250° C. to about 300° C. under higher pressures of about 700 psi. The reaction may optionally employ an organic solvent and use a phase transfer catalyst. Additionally the reaction may optionally be run in the presence of a drying agent for the reduction of water.

DETAILED DESCRIPTION OF THE INVENTION

α-Methylenelactones, α-substituted hydrocarbylidene lactones and particularly α-methylene-γ-butyrolactone are useful as key monomers in both homopolymers and copolymers.

This invention pertains to a method to produce α-methylenelactones. (Scheme 1)

Scheme 1

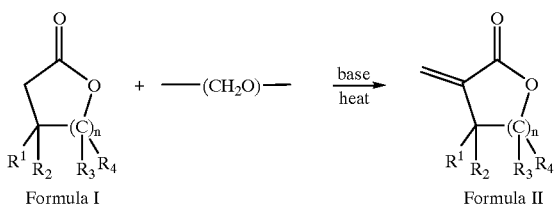

Formula I          Formula II wherein, n=1–11;

$R^1$, $R^2$, $R^3$ and $R^4$ taken independently are hydrogen, hydrocarbyl or substituted hydrocarbyl, $C_1$–$C_{18}$ unsubstituted or substituted alkyl, unsubstituted or substituted alkenyl, unsubstituted or substituted cylcoalkyl, unsubstituted or substituted cylcoalkyl containing at least one heteroatom, unsubstituted or substituted aromatic ring, and unsubstituted or substituted aromatic ring containing at least one heteroatom.

The invention further pertains to a method to produce α-substituted hydrocarbylidene lactones (Scheme 2)

Scheme 2

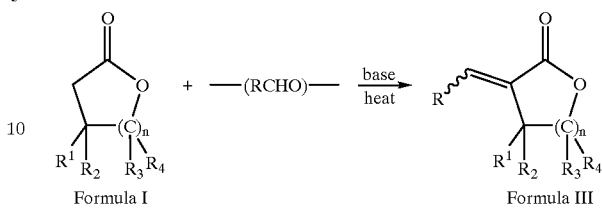

Formula I          Formula III wherein, n=1–11;

R is hydrocarbyl or substituted hydrocarbyl; and $R^1$, $R^2$, $R^3$ and $R^4$ taken independently are hydrogen, hydrocarbyl or substituted hydrocarbyl, $C_1$–$C_{18}$ unsubstituted or substituted alkyl, unsubstituted or substituted alkenyl, unsubstituted or substituted cylcoalkyl, unsubstituted or substituted cylcoalkyl containing at least one heteroatom, unsubstituted or substituted aromatic ring, and unsubstituted or substituted aromatic ring containing at least one heteroatom.

When a group contains a substituent which can be hydrogen, for example $R^1$, $R^2$, $R^3$ and $R^4$, then, when this substituent is taken as hydrogen, it is recognized that this is equivalent to said group being unsubstituted.

The present method proceeds by contacting the instant lactones at a suitable temperature in the presence of a base to give the resultant α-methylenelactones and α-substituted hydrocarbylidene lactones. The reaction may optionally be carried out using an organic solvent and phase transfer catalysts. Where water in the reaction is an issue, a drying agent may also be added.

In the context of this disclosure, a number of terms and abbreviations shall be utilized. The following definitions are provided.

The term "alkyl" includes straight-chain or branched alkyl, such as, methyl, ethyl, n-propyl, i-propyl, or the different butyl, pentyl and hexyl isomers. Also included are all isomers up to and including octadecyl.

"α-methylene-γ-butyrolactone" is abbreviated MBL

"γ-butyrolactone" is abbreviated GBL

"Gas chromatography" is abbreviated GC.

"Nuclear magnetic resonance" is abbreviated NMR.

"Molecular weight" is abbreviated MW.

As used herein the term "formaldehyde derivative" means a compound having the general formula RCHO.

A "hydrocarbyl group" is a univalent group containing only carbon and hydrogen. If not otherwise stated, it is preferred that hydrocarbyl groups herein contain 1 to about 30 carbon atoms.

By "substituted hydrocarbyl" herein is meant a hydrocarbyl group which contains one or more substituent groups which are inert under the process conditions to which the compound containing these groups is subjected. The substituent groups also do not substantially interfere with the process. If not otherwise stated, it is preferred that substituted hydrocarbyl groups herein contain 1 to about 30 carbon atoms. Included in the meaning of "substituted" are heteroaromatic rings.

The term "homogeneous catalyst" are base catalysts of the present invention which are in soluble form and exists in the same phase (solid, liquid or gas) as the reactants.

The term "heterogeneous catalyst" refers to a base catalyst of the present invention which operates on reactions taking place on surfaces where the reacting species are held on the surface of the catalyst by adsorption. Typically heterogeneous catalysts are not in solution and do not exist in the same phase (solid, liquid or gas) as the reactants.

Formaldehyde and Formaldehyde Derivatives

One component of the invention is formaldehyde. Formaldehyde may be supplied in a variety of forms including as a solution or in the form of a formaldehyde polymer. Polymers of formaldehyde are more generally denominated polyacetals and include or are characterized by a linear polymer chain containing recurring —(CH$_2$O)— units or groups. The preferred polymer of formaldehyde in the composition of the invention is polyoxymethylene which has not been stabilized against thermal degradation as, for example, by end-capping the ends of the linear polymer chain with stabilizing end-groups. Thus, a preferred polymer of formaldehyde is paraformaldehyde, which is a lower molecular weight linear polymer available commercially as a fine powder. Another suitable polymer of formaldehyde is, for example, trioxane. Polymers of formaldehyde are described generally in U.S. Pat. No. 2,768,994. Another variety of polymers are sold under the registered trademark Delrin® acetal resins by E. I. du Pont de Nemours and Company, Inc. Delrin® acetal resin polymers usually have been stabilized against thermal degradation but these polymers may still be utilized in the instant invention, as described in Example 9.

The invention may also proceed where a formaldehyde derivative is used in place formaldehyde. One group of suitable formaldehyde derivatives are the substituted aldehydes. When formaldehyde is employed in the reaction the group added to the compound of Formula I, (Scheme 1) will be a methylene group. However, if an alkyl-substituted aldehyde is used, e.g., RCHO, the new group will be an alkyl-substituted hydrocarbylidene group, that is, RCH=. Examples of suitable substituted aldehydes are acetaldehyde, propionaldehyde, butyraldehyde, isobutyraldehyde, n-pentanal, 2-methylbutanal, 3-methylbutanal, n-hexanal, 2-methylpentanal, 3,3-dimethylbutanal, 2-ethylhexanal, 2-methyldecanal, and also dialdehydes such as glyoxal, methylglyoxal, malonic dialdehyde, succinic dialdehyde and glutaric dialdehyde, and other aldehydes such as 3-hydroxy-2,2-dimethylpropanol (hydropivalaldehyde), methoxypivalaldehyde, butoxypivalaldehyde, 4-acetoxybutyaldehyde and 5-formylvaleraldehyde.

Base Catalyst

The basic catalysts are selected from the metal oxides, hydroxides, carbonates and phosphates. The oxides, hydroxides, carbonates and phosphates employed herein may be used as powders, granules, or other particulate forms, or may be supported on an essentially inert support as is common in the art of catalysis. Representative catalysts include but are not limited to potassium carbonate, cesium carbonate, sodium carbonate, barium carbonate, sodium hydrogen carbonate, magnesium oxide, barium oxide, barium hydroxide, lanthanum oxide, potassium hydroxide, cadmium oxide, rubidium oxide, lithium hydroxide, strontium hydroxide, sodium hydroxide, calcium hydroxide, potassium hydroxide, potassium phosphate and mixtures thereof.

The preferred base is potassium carbonate, cesium carbonate or potassium phosphate. The required contact time will depend on the contact temperature. At atmospheric pressures the temperature of the reaction can range from about 70° C. to about 160° C., with a preferred range of about 120° C. to about 140° C. The process of the present invention may be run at higher temperatures by applying pressures greater than atmospheric. For example, where the pressure is varied from about 1 to about 100 atmospheres, or up to about 2000 psi, the reaction may be run at temperatures of greater than 70° C. for higher conversions. Under these conditions temperatures of about 250° C. to about 300° C. and pressures of about 700 psi are preferred. Pressures in the range of 1 to 100 atmospheres, or up to about 2000 psi, will ensure the reactants are maintained in liquid phase.

Additionally the present reaction may make use of heterogeneous catalysts to effect the conversion of lactones to α-methylenelactones and α-substituted hydrocarbylidene lactones. Such catalysts are common and well known in the art (see for example, Hodnett et al., Heterogeneous catalysis, Stud. Surf. Sci. Catal. (1999), 123(Catalysis: An Integrated Approach (2$^{nd}$ edition)), 209–287, hereby incorporated by reference). Suitable heterogeneous catalyst—support—promoter combinations include but are not limited to BaO/SiO2, Ba/1%K/SiO2, Ba/1%Na/SiO2 Ba/1%Au/SiO2, Ba/1%Re/SiO2, Ba/1%Fe/SiO2, Ba/1%Cr/SiO2, KCO3, Li/SiO2, Cs/SiO2, BaO/SiO2, Ba/1%K/SiO2, Ba/1%Na/SiO2, where the base and metal promoter are provided in the form of hydroxides, oxides, carbonates and phosphates.

In some cases reaction conditions may result in the decrease of catalytic efficiency. In these situations it may be useful to modify the reaction process to allow for catalyst regeneration. For example, contacting the present catalysts with O$_2$ at elevated temperatures has the effect of reactivating the catalyst. Contact temperatures with O$_2$ may range from about 300° C. to about 500° C. where temperatures of about 400° C. to about 425° C. are preferred.

The metal oxide, hydroxide, carbonate and phosphate catalysts of the present invention may further comprise catalyst additives and promoters which will enhance the efficiency of the catalyst. Use of theses materials are common and well known in the art (see for example, Kirk-Othmer *Encyclopedia of Chemical Technology*, Howe-Grant Ed., Vol. 5, pp 326–346, (1993), John Wiley & Sons, New York and Ullmann's *Encyclopedia of Industrial Chemistry*, Vol. A5, Gerhartz et al., Eds., pp. 337–346, (1986), VCH Publishers, New York, both hereby incorporated by reference.) Particularly useful in the present invention are promoters which include, but are not limited to Au, Na, K, Cs, Re, Fe, and Cr. The relative percentages of the catalyst promoter may vary. Useful amounts of promoter will be from about 0.01% to about 5.00% by weight of catalyst.

Basic catalysts of the present invention may be supported or unsupported. Where a support is desired suitable supports include but are not limited to silica, titania, zirconia, alumina, carbon, various zeolites and mixtures thereof.

Phase Transfer Catalyst and Solvent Systems

The present method may optionally employ an organic solvent. Suitable organic solvents include but are not limited to toluene, isopropanol, methanol, acetonitrile, 2,2-diethoxypropane, n-butanol and polyethylene glycols. The preferred solvent for use in the present invention is toluene.

Where a solvent is employed the instant invention may optionally also use a phase transfer catalyst. Although a wide variety of phase transfer catalysts are known and used in the chemical industry, certain phase transfer catalysts work more effectively than others for a particular chemical reaction and for individual reactants. A phase transfer catalyst such as tetrabutylammonium bromide, can be employed in the reaction(s). Other catalysts useful herein include but are not limited to quaternary ammonium salts, quaternary phosphonium salts, crown ethers, and polyethers. For polyethers, the phase transfer catalyst is a member selected from the group consisting of polyethylene glycols (PEG's) of various molecular weights (MW). PEG's with an average molecular weight from 200 to >20,000 are available commercially. The number of repeat units, n, in the PEG is an important factor in its effectiveness as a phase transfer catalyst. Values of n greater than or equal to 8 are generally preferred as phase transfer catalysts. The phase transfer catalyst is used in an amount of 0 to 0.25 parts, preferably 0.05 to 0.10 parts, per part by weight of the reactive substrate. Phase transfer catalysts are common and well known in the art, see for example, Cook et al., *Chim. Oggi* 16(1/2):44–48 (1998) ;"Phase Transfer Catalysis: Fundamentals, Applications, and Industrial Perspectives" by C. M. Starks, C. L. Liotta, and M. Halpern., Chapman & Hall, Inc. 1994.

Drying Agents

In the instant invention, the addition of a drying agent in reactions can increase the conversion of starting material to product by removing water. Suitable drying agents include but are not limited to anhydrous sodium sulfate, anhydrous magnesium sulfate, molecular sieves (various pore sizes), calcium oxide, calcium chloride, potassium carbonate, oxazolidines, orthoesters and mixtures thereof. The preferred drying agent is potassium carbonate. Where a drying agent cannot be used, water can also be removed by azeotropic distillation.

Recovery Methods

The desired products, including α-methylene-γ-butyrolactone, are recovered using techniques common to the art. For example, when allowed to cool the α-methylene-γ-butyrolactone reaction mixture forms a viscous, clear mass. Alternatively, when heated under vacuum, the α-methylene-γ-butyrolactone/γ-butyrolactone mixture can be distilled directly from the reaction mixture. Additionally, the reaction mixture can be dissolved in water, adjusted to pH=4 with 6N HCl, then distilled. Similarly, the separation of α-methylene-γ-butyrolactone from γ-butyrolactone can be accomplished using vacuum distillation with a spinning band column. Additionally the α-methylene-γ-butyrolactone of the present invention may be recovered and purified by a depolymerization process. For example a solution of MBL in GBL containing a free radical initiator (for example, VAZO 64™ or VAZO 67™ [E. I. du Pont de Nemours and Company, Wilmington DE]) is fed continuously in to a heated reactor containing GBL. The MBL/GBL solution is fed slowly to control the polymerization exotherm. The MBL polymer is isolated by precipitation in to a non-solvent (typically methanol) and recovered by filtration. The polymer is then heated under vacuum at temperatures greater than about 320° C. to recover MBL monomer.

Alternatively MBL can be isolated by steam distillation. Typically, steam is allowed to flow through a distillation apparatus containing MBL. The water distillate (containing MBL) is then extracted with an organic solvent such as ethyl acetate. The solvent is then removed in vacuo to recover MBL.

In another recovery method MBL can also be purified by melt crystallization. In this process, MBL is cooled below its melting point (below about 35° C.) to form a solid. GBL and other impurities are liquids at that temperature and are allowed to flow away from the pure, solid MBL. The temperature is then raised to melt the MBL and recover it in a more pure form. The melt crystallization process can be repeated to obtain high purity MBL.

Reaction Conditions and Processes

The present method lends itself to either batch or continuous processes. In the case of α-methylene-γ-butyrolactone preparation, a continuous process employs a pipeline reactor for the γ-butyrolactone to α-methylene-γ-butyrolactone conversion. Liquid γ-butyrolactone is fed into a pipe containing two reagent beds. In the first bed, γ-butyrolactone becomes saturated with formaldehyde (gas) by passing liquid γ-butyrolactone over paraformaldehyde at a suitable temperature. The solution then continues on to a catalyst bed (e.g., potassium carbonate) where the reaction occurs to make α-methylene-γ-butyrolactone. Any off-gases are vented out the end of the pipeline and the α-methylene-γ-butyrolactone /γ-butyrolactone solution falls out as a liquid. If needed, the mixture can be fed into the pipeline again to increase the overall conversion to α-methylene-γ-butyrolactone.

It is recognized that some reagents and reaction conditions described for preparing compounds of Formula II and Formula III may not be compatible with certain functionalities present in the lactone starting material (Formula I). In these instances, the incorporation of protection/deprotection sequences or functional group interconversions into the synthesis will aid in obtaining the desired products. The use and choice of the protecting groups will be apparent to one skilled in chemical synthesis (see, for example, Greene, T. W.; Wuts, P. G. M. *Protective Groups in Organic Synthesis*, $2^{nd}$ ed.; Wiley: New York, 1991). One skilled in the art will recognize that, in some cases, after the introduction of a given reagent as it is depicted in any individual scheme, it may be necessary to perform additional routine synthetic steps not described in detail to complete the synthesis of compounds of Formula II and Formula III. One skilled in the art will also recognize that it may be necessary to perform a combination of the steps illustrated in the above schemes in an order other than that implied by the particular sequence presented to prepare the compounds of Formula II and Formula III.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usage and conditions.

Common reagents were purchased from Sigma-Aldrich and solvents from VWR Scientific. NMR spectra were recorded on a Varian VXR-500 spectrometer. Gas chromatography (GC) was performed on a Hewlett-Packard 6890 series instrument running HP Chemstation® software and equipped with an HP-5 (5% Phenyl Methyl Siloxane) column. Pure α-methylene-γ-butyrolactone was synthesized using the method reported by Murray (*Synthesis* 1:35–38 (1985)) for use in GC methods. α-Methylene-γ-butyrolactone was purified by distillation at 0.5 torr/65° C. to give a colorless liquid: $^1$H NMR (500 MHz, CDCl$_3$)δ2.9 (m, 2H), 4.3 (t, J=5.2, 2H), 5.6 (t, J=2.5, 1H), 6.2 (t, J=3.2, 1H); $^{13}$C NMR (125 MHz, CDCl$_3$)δ171.49, 134.40, 122.98, 66.06, 28.16. $^1$H NMR spectra are reported in ppm downfield from tetramethylsilane; s=singlet, d=doublet, and br s=broad singlet.

Where indicated below, GC was used to determine % product relative to % starting material. With GC, response factors were assumed to be the same for both product and starting material. In addition to GC, NMR was also used to determine the relative percentages of product to starting material (data not shown).

The meaning of abbreviations is as follows: "µL" means microliter, "ml" means milliliter(s), "L" means liter(s), "mM" means millimolar, "M" means molar, "mmol" means millimole(s) and "ng" means nanogram(s).

Example 1

Preparation of α-Methylene-γ-butyrolactone

A 1 L flask was charged with anhydrous toluene (200 mL) and potassium carbonate (28.6 g, 0.22 mol). The mixture was stirred for one h before adding tetrabutylammonium bromide (4.5 g, 0.014 mol), γ-butyrolactone (6.3 g, 0.07 mol), and paraformaldehyde (10.5 g, 0.35 mol). The mixture was brought to reflux and stirred for one hour. The reaction was checked by GC and contained 7% α-methylene-γ-butyrolactone in γ-butyrolactone.

Example 2

Preparation of α-Methylene-γ-butyrolactone from γ-Butyrolactone

A 1 L 3-neck flask equipped with a mechanical stirrer, condenser, and thermometer was charged with anhydrous toluene (300 mL) and potassium carbonate (96 g, 0.7 mol). After stirring for one h, tetrabutylammonium iodide (26 g, 0.07 mol), γ-butyrolactone (20 g, 0.23 mol), and paraformaldehyde (35 g, 1.16 mol) were added. The mixture was heated to 80° C. and stirred vigorously for one hour. The reaction was checked by GC and contained 20% α-methylene-γ-butyrolactone in γ-butyrolactone.

Example 3

Preparation of α-Methylene-γ-butyrolactone from γ-Butyrolactone

A 1 L 3-neck flask equipped with a mechanical stirrer, condenser, and thermometer was charged with anhydrous toluene (200 mL) and potassium carbonate (80 g, 0.58 mol). After stirring for one hour, tricaprylmethylammonium chloride (Aliquat 336) (4.7 g, 0.01 mol), γ-butyrolactone (10 g, 0.12 mol), and paraformaldehyde (17.4 g, 0.58 mol) were added. The mixture was heated at reflux and stirred vigorously for eight hours. The reaction was checked by GC and contained 25% α-methylene-γ-butyrolactone in γ-butyrolactone.

Example 4

Preparation of α-Methylene-γ-butyrolactone from γ-Butyrolactone

A 1 L 3-neck flask equipped with a mechanical stirrer, condenser, and thermometer was charged with anhydrous toluene (200 mL) and potassium carbonate (96 g, 0.58 mol). After stirring for one hour, tricaprylmethylammonium chloride (Aliquat 336) (4.7 g, 0.01 mol), γ-butyrolactone (20 g, 0.12 mol), magnesium sulfate (31 g, 0.26 mol), and paraformaldehyde (35 g, 1.2 mol) were added. The mixture was heated at reflux and stirred for twelve hours. The reaction was checked by GC and contained 20% α-methylene-γ-butyrolactone in γ-butyrolactone.

Example 5

Preparation of α-Methylene-γ-butyrolactone from γ-Butyrolactone

A 1 L 3-neck flask equipped with a mechanical stirrer and a Dean-Stark trap charged with anhydrous toluene (250 mL), polyethylene glycol dimethyl ether (MW 1000) (11.6 g), and potassium carbonate (160 g, 1.2 mol). The mixture was heated at reflux (oil bath temperature 140° C.) for one hour with vigorous stirring. During this time, approximately 2 mL of water collected in the Dean-Stark trap. The mixture was allowed to cool under nitrogen before γ-butyrolactone (20 g, 0.12 mol), magnesium sulfate (31 g, 0.26 mol), and paraformaldehyde (35 g, 1.2 mol) were added. The mixture was heated at 120° C. and stirred vigorously for six hours. The reaction was checked by GC and contained 32% α-methylene-γ-butyrolactone in γ-butyrolactone.

Example 6

Preparation of α-Methylene-γ-butyrolactone from γ-Butyrolactone

Example 5 was repeated with the exception that the PEG 1000 was not pre-dried by azeotropic distillation. After six hours the reaction was checked by GC and contained 11% α-methylene-γ-butyrolactone in γ-butyrolactone.

Example 7

Preparation of α-Methylene-γ-butyrolactone from γ-Butyrolactone

A 500 mL 3-neck flask equipped with a mechanical stirrer and a Dean-Stark trap charged with γ-butyrolactone (150 g, 1.74 mol), polyethylene glycol (MW 1000) dimethyl ether (4.4 g), anhydrous potassium carbonate (180 g, 1.3 mol), and paraformaldehyde (78 g, 2.6 mol). The mixture was heated at 100° C. and stirred vigorously for two hours. The reaction was checked by GC and contained 18% α-methylene-γ-butyrolactone in γ-butyrolactone.

Example 8

Preparation of α-Methylene-γ-butyrolactone from γ-Butyrolactone

A 500 mL 3-neck flask equipped with a mechanical stirrer and a Dean-Stark trap charged with γ-butyrolactone (150 g, 1.74 mol), anhydrous potassium carbonate (60 g, 0.44 mol), and paraformaldehyde (78 g, 2.6 mol). The mixture was heated at 100° C. and stirred vigorously for two hours. The reaction was allowed to cool and an additional amount of paraformaldehyde (78 g, 2.6 mol) was added and the reaction heated at 100° C. with vigorous stirring. The reaction was checked by GC and contained 34% α-methylene-γ-butyrolactone in γ-butyrolactone.

Example 9

Preparation of α-Methylene-γ-butyrolactone from γ-Butyrolactone

A 250 mL flask equipped with a mechanical stirrer and thermocouple was charged with γ-butyrolactone (100 g, 1.16 mol) and anhydrous potassium carbonate. The mixture was heated at 130° C. and stirred vigorously while flowing excess formaldehyde gas over the reaction mixture. The anhydrous formaldehyde gas was generated from thermally cracking formyl acetal of 2-ethylhexanol (process utilized for Delrin® acetal resin polymers, available for E. I. du Pont de Nemours and Company of Wilmington, Del., USA). After one hour, the reaction was checked by GC and contained 10% α-methylene-γ-butyrolactone in γ-butyrolactone.

Example 10

Preparation of α-Methylene-γ-butyrolactone from γ-Butyrolactone

γ-Butyrolactone was vacuum distilled from magnesium sulfate and stored over 4-molecular sieves. Potassium carbonate was dried overnight at 120° C. A 500 mL 3-neck flask equipped with a mechanical stirrer and a distillation head was charged with γ-butyrolactone (150 g, 1.74 mol), anhydrous potassium carbonate (60 g, 0.44 mol), and paraformaldehyde (52 g, 1.7 mol). The mixture was heated at 130° C. and stirred vigorously for 1 hour. The reaction was checked by GC and contained 52% α-methylene-γ-butyrolactone in γ-butyrolactone.

Example 11

Preparation of α-Methylene-γ-butyrolactone from γ-Butyrolactone

A 1 L 3-neck flask equipped with a mechanical stirrer and a distillation head was charged with γ-butyrolactone (100 g, 1.2 mol), anhydrous cesium carbonate (57 g, 0.17 mol), and paraformaldehyde (32 g, 1.2 mol). The mixture was heated at 130° C. and stirred vigorously for 30 minutes. The reaction was allowed to cool before adding additional cesium carbonate (50 g, 0.15 mol) and paraformaldehyde (32 g, 1.2 mol). The reaction was heated to 130° C. and stirred for one hour. The reaction was checked by GC and contained 65% α-methylene-γ-butyrolactone in γ-butyrolactone.

Example 12

Increasing the α-Methylene-γ-butyrolactone Concentration by a Two Step Process

A 1000 mL 3-neck flask equipped with a mechanical stirrer and a distillation head was charged with 125 grams of a 65% MBL in α-methylene-γ-butyrolactone solution (see Example 11). To this was added anhydrous potassium carbonate (53 g, 0.40 mol), and paraformaldehyde (46 g, 1.5 mol) and the mixture was heated at 130° C. and stirred vigorously for two hours. The reaction was checked by GC and contained 78 weight % α-methylene-γ-butyrolactone in γ-butyrolactone.

Example 13

Preparation of α-Methylene-γ-butyrolactone from γ-Butyrolactone

A 1000 mL 3-neck flask equipped with a mechanical stirrer and a distillation head was charged with γ-butyrolactone (150 g, 1.74 mol), anhydrous potassium carbonate (180 g, 1.3 mol), and paraformaldehyde (104 g, 3.5 mol), and 200 mL of polyethylene glycol (MW 900). The mixture was heated at 130° C. and stirred vigorously for 30 minutes. The reaction was checked by GC and contained 60 weight % α-methylene-γ-butyrolactone in γ-butyrolactone.

Example 14

Preparation of α-Methylene-δ-valerolactone from δ-Valerolactone

A 500 mL 3-neck flask equipped with a mechanical stirrer and a distillation head was charged with δ-valerolactone (53 g, 0.53 mol), anhydrous potassium carbonate (21 g, 0.15 mol), and paraformaldehyde (18 g, 0.62 mol). The mixture was heated at 130° C. and stirred vigorously for 1 hour. The reaction was checked by GC and contained 35 weight % α-methylene-δ-valerolactone in δ-butyrolactone.

Example 15

Preparation of α-Methylene-γ-butyrolactone from γ-Butyrolactone—Continuous Process A 200 mL flask equipped was charged with γ-butyrolactone (100 g, 1.16 mol) and paraformaldehyde (38 g, 1.26 mol). The suspension was then heated to 100° C. and poured through a fritted glass funnel containing anhydrous potassium carbonate (450 g, 3.26 mol). The filtrate was checked by GC and contained 11 weight % α-methylene-γ-butyrolactone in γ-butyrolactone.

Example 16

Preparation of α-Methylene-γ-butyrolactone from γ-Butyrolactone—Use of Potassium Phosphate A 125 mL quartz shaker tube was charged with γ-butyrolactone (30 g, 0.35 mol), anhydrous potassium phosphate (180 g, 0.034 mol), and paraformaldehyde (10.5 g, 0.35 mol). The tube was heated at 125° C. in a pressure vessel and shaken for one hour. The reaction was checked by GC and contained 26 weight % α-methylene-γ-butyrolactone in γ-butyrolactone.

Example 17

Preparation of α-Methylene-γ-butyrolactone from γ-Butyrolactone—Use of 2-ethylhexylhemiformal as the formaldehyde source A 125 mL quartz shaker tube was charged with γ-butyrolactone (10 g, 0.11 mol), anhydrous potassium carbonate (48.1 g, 0.35 mol), and 2-ethylhexylhemiformal, a 20% solution in 2-ethylhexanol, (22.3 g, 0.15 mol equivalents formaldehyde). The tube was heated at 135° C. in a pressure vessel and shaken for three hours. The reaction was checked by GC and contained 36 weight % α-methylene-γ-butyrolactone in γ-butyrolactone.

Example 18

Preparation of α-Methylene-γ-butyrolactone from γ-Butyrolactone in n-Butanol

A 500 mL flask equipped with a mechanical stirrer, thermometer, dean-stark trap, and condenser was charged with γ-butyrolactone (150 g, 1.74 mol), anhydrous potassium carbonate (60.2 g, 0.43 mol), n-butanol (100 mL), and paraformaldehyde (57.6 g, 1.92 mol). The mixture was heated to reflux (pot temp. 120° C., head temp. 88° C.) and stirred vigorously for 60 minutes. The reaction was checked by GC and contained 45% α-methylene-γ-butyrolactone in γ-butyrolactone.

TABLE 1

Example 19
Use Of Heterogeneous Catalyst At High Pressure For The Conversion Of GBL To MBL

| Time (hrs) | Temp (C.) | N2 Press (psi) | Feedstock | Base Catalyst[4] | MBL Sel (%) | GBL Con (%) | Feedstock | Base (mg) |
|---|---|---|---|---|---|---|---|---|
| 2 | 225 | 700 | GBL + FA[1] | Ba/SiO2 | <1% | nd[3] | 1 ml | 101.70 |
| 2 | 225 | 700 | GBL + FA | 10%Ba/1%K/SiO2 | <1% | nd | 1 ml | 107.50 |

TABLE 1-continued

Example 19
Use Of Heterogeneous Catalyst At High Pressure For The Conversion Of GBL To MBL

| Time (hrs) | Temp (C.) | N2 Press (psi) | Feedstock | Base Catalyst[4] | MBL Sel (%) | GBL Con (%) | Feedstock | Base (mg) |
|---|---|---|---|---|---|---|---|---|
| 2 | 225 | 700 | GBL + FA | 10%Ba/1%Na/SiO2 | <1% | nd | 1 ml | 102.20 |
| 2 | 225 | 700 | GBL + FA | 10%Ba/1%Au/SiO2 | <1% | nd | 1 ml | 98.10 |
| 2 | 225 | 700 | GBL + FA | 10%Ba/1%Re/SiO2 | <1% | nd | 1 ml | 108.60 |
| 2 | 225 | 700 | GBL + FA | 10%Ba/1%Fe/SiO2 | <1% | nd | 1 ml | 97.60 |
| 2 | 225 | 700 | GBL + FA | 10%Ba/1%Cr/SiO2 | <1% | nd | 1 ml | 103.50 |
| 2 | 225 | 700 | GBL + FA | K2CO3 | <1% | nd | 1 ml | |
| 2 | 150 | 700 | GBL + PFA[2] | K2CO3 | 19.48% | 71.05% | 928.40 mg | 423.20 |
| 2 | 150 | 700 | GBL + PFA | Li/SiO2 | 6.92% | 47.82% | 973.90 mg | 105.30 |
| 2 | 150 | 700 | GBL + PFA | Cs/SiO2 | 2.31% | 9.20% | 955.90 mg | 100.90 |
| 2 | 150 | 700 | GBL + PFA | Ba/SiO2 | 0.56% | 9.50% | 993.50 mg | 97.20 |
| 2 | 150 | 700 | GBL + PFA | 10%Ba/1%K/SiO2 | 17.49% | 25.07% | 987.10 mg | 102.70 |
| 2 | 150 | 700 | GBL + PFA | 10%Ba/1%Na/SiO2 | 23.04% | 19.50% | 991.30 mg | 101.00 |

[1]FA = 8:1 Formaldehyde:GBL using formalin solution
[2]PFA = paraformaldehyde
[3]nd = Not Done
[4]Base and metal promoters are supplied in the form of oxides, hydroxides, carbonates or phosphates Example 19 illustrates that a heterogeneous catalyst may be used to effect the conversion of a lactone to an α-methylenelactone. Here GBL was heated and passed over a catalyst in the heterogeneous state in the presence of either formaldehyde or paraformaldehyde at 700 psi for the production of MBL. Selectivities of MBL ranged from about 1% to about 23% and depending on the catalyst used.

What is claimed is:

1. A process for preparing α-methylenelactones of Formula II comprising heating lactones of Formula I and formaldehyde in the presence of a base:

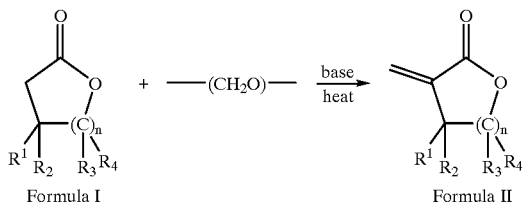

wherein, n=1–11;

$R^1$, $R^2$, $R^3$ and $R^4$ taken independently are hydrogen, $C_1$–$C_{30}$ unsubstituted or substituted alkyl, unsubstituted or substituted alkenyl, unsubstituted or substituted cylcoalkyl, unsubstituted or substituted cylcoalkyl containing at least one heteroatom, unsubstituted or substituted aromatic ring, and unsubstituted or substituted aromatic ring containing at least one heteroatom;

to form a reaction mixture; and optionally recovering the α-methylenelactones of Formula II.

2. A process according to claim 1 wherein any two of $R^1$, $R^2$, $R^3$ and $R^4$ form a ring structure selected from the group consisting of, unsubstituted or substituted cylcoalkyl, unsubstituted or substituted cylcoalkyl containing at least one heteroatom in the ring, unsubstituted or substituted aromatic ring, and unsubstituted or substituted aromatic ring containing at least one heteroatom in the ring.

3. A process according to claim 1 wherein the lactone of Formula I is γ-butyrolactone and the α-methylenelactone of Formula II is α-methylene-γ-butyrolactone.

4. A process according to claim 1 wherein $R^3$ is $CH_3$.

5. A process according to claim 1 wherein the base is selected from the group consisting of metal oxides, hydroxides, carbonates and phosphates and mixtures thereof.

6. A process according to claim 5 wherein the base is selected from the group consisting of potassium carbonate, cesium carbonate, sodium carbonate, barium carbonate, sodium hydrogen carbonate, magnesium oxide, barium oxide, barium hydroxide, lanthanum oxide, potassium hydroxide, cadmium oxide, rubidium oxide, lithium hydroxide, strontium hydroxide, sodium hydroxide, calcium hydroxide, potassium hydroxide, potassium phosphate and mixtures thereof.

7. A process according to claim 6 wherein base is selected from the group consisting of lithium hydroxide, potassium hydroxide, sodium hydroxide and potassium phosphate.

8. A process according to claim 1 wherein the base catalyst is optionally supported on a suitable support.

9. A process according to claim 6 wherein the base catalyst optionally contains a catalyst promoter comprising a metal or metal salt.

10. A process according to claim 9 wherein said catalyst promoter comprises a metal selected from the group consisting of Au, Na, K, Cs, Re, Fe, and Cr.

11. A process according to claim 10 wherein the concentration of the promoter is from about 0.01% to about 5.0o% by weight of catalyst.

12. A process according to claim 8 wherein the suitable support is selected from the group consisting of silica, titania, zirconia, alumina, carbon, zeolites and mixtures thereof.

13. A process according to claim 1 wherein the formaldehyde is supplied in a form selected from the group consisting of formalin, 2-ethylhexylhemiformal, paraformaldehyde, trioxane, acetals and polyacetals.

14. A process according to claim 1 wherein the temperature is at least about 70° C. and the pressure is less than or equal to 2000 psi.

15. A process according to claim 14 wherein the temperature is about 120° C. to about 140° C. and the pressure is atmospheric.

16. A process according to claim 1 wherein the temperature is at about 250° C. to about 300° C. and the pressure is about 700 psi.

17. A process according to claims 1, 5, 6 or 9 wherein the base is a homogeneous catalyst.

18. A process according to any one of claims 1, 5, 6 or 9 wherein the base is a heterogeneous catalyst.

19. A process according to claim 1 wherein the conversion of lactones to α-methylenelactones occurs in the presence of an organic solvent.

20. A process according to claim 19 wherein the organic solvent is selected from the group consisting of toluene, isopropanol, methanol, acetonitrile, 2,2-diethoxypropane, n-butanol and polyethylene glycols.

21. A process according to claim 1 wherein a phase transfer catalyst is employed.

22. A process according to claim 21 wherein the phase transfer catalyst is selected from the group consisting of quaternary ammonium salts, quaternary phosphonium salts, crown ethers, and polyethers.

23. A process according to claim 1 wherein a drying agent is employed.

24. A process according to claim 23 wherein the drying agent is selected from the group consisting of anhydrous sodium sulfate, anhydrous magnesium sulfate, 4 Å molecular sieves, calcium oxide, calcium chloride, potassium carbonate, oxazolidines, orthoesters and mixtures thereof.

25. A process for preparing alkyl-substituted methylene lactones of Formula III comprising heating lactones of Formula I and a formaldehyde derivative in the presence of a base:

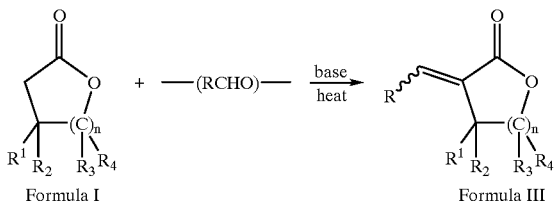

wherein, n=1–11;

R is hydrocarbyl or substituted hydrocarbyl; and $R^1$, $R^2$, $R^3$ and $R^4$ taken independently are hydrogen, $C_1$–$C_{30}$ unsubstituted or substituted alkyl, unsubstituted or substituted alkenyl, unsubstituted or substituted cylcoalkyl, unsubstituted or substituted cylcoalkyl containing at least one heteroatom, unsubstituted or substituted aromatic ring, and unsubstituted or substituted aromatic ring containing at least one heteroatom;

to form a reaction mixture; and optionally recovering the α-methylenelactones of Formula III.

26. A process according to claim 25 wherein any two of $R^1$, $R^2$, $R^3$ and $R^4$ optionally form a ring structure selected from the group consisting of, unsubstituted or substituted cylcoalkyl, unsubstituted or substituted cylcoalkyl containing at least one heteroatom in the ring, unsubstituted or substituted aromatic ring, and unsubstituted or substituted aromatic ring containing at least one heteroatom in the ring.

27. A process according to claim 25 wherein the formaldehyde derivative is a substituted aldehyde.

28. A process according to claim 27 wherein the substituted aldehyde is selected from the group consisting of acetaldehyde, propionaldehyde, butyraldehyde, isobutyraldehyde, n-pentanal, 2-methylbutanal, 3-methylbutanal, n-hexanal, 2-methylpentanal, 3,3-dimethylbutanal, 2-ethylhexanal, 2-methyldecanal, glyoxal, methylglyoxal, malonic dialdehyde, succinic dialdehyde and glutaric dialdehyde, 3-hydroxy-2,2-dimethylpropanol, methoxypivalaldehyde, butoxypivalaldehyde, 4-acetoxybutyaldehyde and 5-formylvaleraldehyde.

29. A process according to claim 25 wherein the base is selected from the group consisting of metal oxides, hydroxides, carbonates, phosphates and mixtures thereof.

30. A process according to claim 29 wherein the base is selected from the group consisting of potassium carbonate, cesium carbonate, sodium carbonate, barium carbonate, sodium hydrogen carbonate, magnesium oxide, barium oxide, barium hydroxide, lanthanum oxide, potassium hydroxide, cadmium oxide, rubidium oxide, lithium hydroxide, strontium hydroxide, sodium hydroxide, calcium hydroxide, potassium hydroxide, potassium phosphate and mixtures thereof.

31. A process according to claim 25 wherein the base is optionally supported on a suitable support.

32. A process according to claim 31 wherein the base optionally comprises a catalyst promoter.

33. A process according to claim 31 wherein the suitable support is selected from the group consisting of silica, titania, zirconia, alumina, carbon, zeolites and mixtures thereof.

34. A process according to claim 25 wherein the temperature is at least about 70° C. and the pressure is less than or equal to 2000 psi.

35. The process according to claim 25 wherein the temperature is at about 250° C. to about 300° C. a and the pressure is about 700 psi.

36. A process according to claim 25 wherein the base is a homogeneous catalyst.

37. A process according to claim 25 wherein the base is a heterogeneous catalyst.

38. A process according to claim 25 wherein the conversion of lactones to α-methylenelactones occurs in the presence of an organic solvent.

39. A process according to claim 25 wherein a phase transfer catalyst is employed.

40. A process according to claim 25 wherein a drying agent is employed.

41. A process according to claim 1 or 25 wherein the α-methylenelactones or alkyl-substituted methylene lactones are recovered by a depolymerization process comprising the steps of:

a) adding a free radical initiator to the reaction mixture at a temperature where α-methylenelactones or alkyl-substituted methylene lactones are polymerized;

b) precipitating the polymerized α-methylenelactones or alkyl-substituted methylene lactones of step (a); and c) heating the precipitated α-methylenelactone or alkyl-substituted methylene lactone polymer to recover the α-methylenelactone or alkyl-substituted methylene lactone monomer.

42. A process according to claim 1 or 25 wherein the α-methylenelactones or alkyl-substituted methylene lactones are recovered by a steam distillation process comprising the steps of:

a) contacting the reaction mixture containing the α-methylenelactones or alkyl-substituted methylene lactones with steam wherein the steam and α-methylenelactones or alkyl-substituted methylene lactones form a mixture;

b) distilling the steam/α-methylenelactone mixture to form a distillate; and c) purifying the α-methylenelactones by either extracting the α-methylenelactones or alkyl-substituted methylene lactones from the distillate with a solvent or performing a second distillation.

43. A process according to claim 1 or 25 wherein the α-methylenelactones or alkyl-substituted methylene lactones are recovered by a melt crystallization process comprising the steps of:

a) cooling the reaction mixture containing the α-methylenelactones or alkyl-substituted methylene lactones and residual lactones below the melting point of the α-methylenelactones or alkyl-substituted methylene lactones wherein the α-methylenelactones or alkyl-substituted methylene lactones attain a solid state and the residual lactones are in a solution state;

b) washing away the residual lactones from the solid α-methylene-lactones or alkyl-substituted methylene lactones; and c) heating the solid α-methylenelactones or alkyl-substituted methylene lactones of step (b) to recover the α-methylene-lactones or alkyl-substituted methylene lactones.

\* \* \* \* \*